United States Patent [19]

Ardecky et al.

[11] Patent Number: 5,086,059

[45] Date of Patent: Feb. 4, 1992

[54] BIS-NAPHTHALIMIDES AS ANTICANCER AGENTS

[75] Inventors: Robert J. Ardecky, Landenberg, Pa.; Arthur D. Patten, Bear; Jung-Hui Sun, Hockessin, both of Del.

[73] Assignee: Du Pont Merck Pharmaceutical Company, Wilmington, Del.

[21] Appl. No.: 539,115

[22] Filed: Jun. 7, 1990

[51] Int. Cl.$^5$ ............... C07D 221/18; A61K 31/435
[52] U.S. Cl. ..................... 514/284; 546/76; 546/77; 546/99
[58] Field of Search .................. 546/77, 99, 76; 514/284

[56] References Cited

U.S. PATENT DOCUMENTS

| | | | |
|---|---|---|---|
| 3,884,924 | 5/1975 | Eiglmeier et al. | 546/76 |
| 4,841,052 | 6/1989 | Harnisch et al. | 544/361 |
| 4,874,863 | 10/1989 | Brana et al. | 546/99 |

Primary Examiner—John M. Ford
Assistant Examiner—Y. N. Gupta

[57] ABSTRACT

There are provided novel bis-napthalimide compounds useful as antitumor agents, pharmaceutical compositions containing them and processes for preparing intermediates to such compounds.

36 Claims, No Drawings

BIS-NAPHTHALIMIDES AS ANTICANCER AGENTS

BACKGROUND OF THE INVENTION

1. Field of the Invention

This invention relates to bis-naphthalimides, processes for their preparation, pharmaceutical compositions containing them, and methods of using them to treat cancer in mammals.

2. Prior Art

Harnisch, et al. in U.S. Pat. No. 4,841,052 issued June 20, 1989 describe naphthalic acid imides of the formula

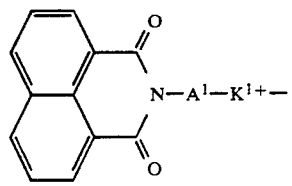

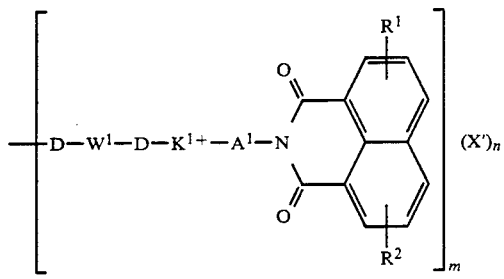

wherein:
$A^1$ represents $C_2$–$C_5$ alkylene;
$K^{1+}$ represents

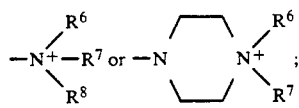

$R^6$ represents $C_1$–$C_{16}$ alkyl, carbamoylmethyl or benzyl;
$R^7$ represents methyl or ethyl or a single bond linked to D;
$R^8$ represents methyl or ethyl;
$W^1$ represents

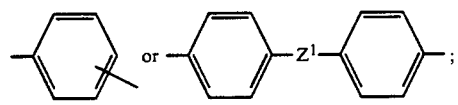

$Z^1$ represents —$CH_2$—, or

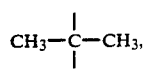

—O— or —$SO_2$—; and
X represents an unsubstituted benzosulphonate or a benzenesulphonate substituted by chlorine or $C_1$–$C_{12}$ alkyl, a $C_5$–$C_{18}$ alkylsulphonate or a salt of a $C_5$–$C_{18}$ alkylcarboxylic acid or a salt of a condensation product of formaldehyde and arylsulphonic acids and/or optionally sulphonated 4,4'-dihydroxydiphenylsulphone, wherein D represents —$CH_2$—, —$CH_2$—CO—, —$CH_2$—CO—HN13 or —$CH_2$—CO—NH—$CH_2$— and m represents 0 or 1.

These compounds are highly suitable as charge-regulating substances in electrophotographic toners.

U.S. Pat. No. 4,874,863 issued Oct. 17, 1989 discloses compounds of the Formula (I)

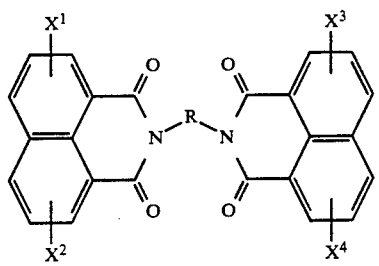

wherein $X^1$, $X^2$, $X^3$ and $X^4$ are identical or different and are each H, $NO_2$, $NH_2$, $C_1$–$C_6$ alkylamino, di-$C_1$–$C_6$ alkylamino, OH, $C_1$–$C_6$ alkoxy, halogen, trihalomethyl, $C_1$–$C_6$ alkyl, formyl, $C_1$–$C_6$ alkylcarbonyl, ureyl, $C_1$–$C_6$ alkylureyl and R is a straight chain or branched $C_4$–$C_{10}$ alkylene which is interrupted at one or two points in the chain by a secondary or tertiary amino group, where 2 nitrogen atoms may additionally be bonded to one another by an alkylene group, or a salt with a physiologically tolerated acid.

SUMMARY OF THE INVENTION

This invention relates to bis-naphthalimide compounds having the Formula (I), pharmaceutical compositions containing these compounds and methods of using these compounds for treating cancer in a mammal.

A compound of the formula:

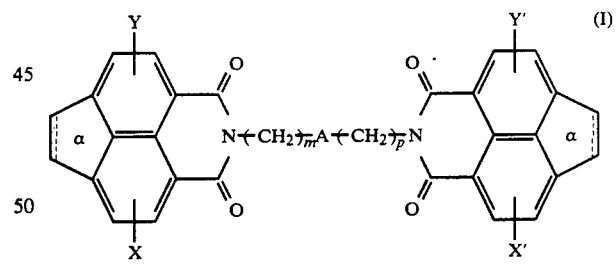

or a pharmaceutically acceptable salt thereof, wherein:
A is $RN(CH_2)_nNR'$ or $NR^1$ (n is 2–10);
R, R' and $R^1$ independently are H, $C_1$–$C_6$ alkyl, benzyl optionally substituted with 1 or more substituents independently selected from the group consisting of:
H, $C_1$–$C_6$ alkyl, halogen, $CF_3$, $NO_2$, OH, $N(R^2)_2$, $OR^3$, $CO_2R^4$, $CONR^5$, $NHCOR^6$, $SO_2NR^7$ or $S(O)_tR^8$, (t is 0, 1 or 2);
$R^2$, $R^5$ and $R^7$ independently are H or $C_1$–$C_3$ alkyl including cyclopropyl;
$R^3$ and $R^4$ independently are H or $C_1$–$C_6$ alkyl;
$R^6$ and $R^8$ independently are $C_1$–$C_6$ alkyl;
X, X', Y and Y' independently are selected from the group consisting of:

H, $NO_2$, $N(R^9)_2$, halogen or $OR^{10}$;
$R^9$ and $R^{10}$ independently are H or $C_1$-$C_6$ alkyl;
each α is independently a single or a double bond; and
m and p independently are 2-10.

Preferred compounds of the present invention are those compounds of Formula (I) wherein:
 A is $RN(CH_2)_nNR'$; and/or
 R and R' are $C_1$-$C_6$ alkyl; and/or
 n is 2-6; and/or
 m and p independently are 2-6; and/or
 X, X', Y and Y' are H; and/or
 each α is a single bond.

Specifically preferred compounds of the present invention are:
 (a) 1,4-Bis-[3-(1,3,6,7-tetrahydro-1,3-dioxo-2H-indeno[6,7,1-def]isoquinoline-2-yl)propylamino]-butane, or the dihydromethane sulfonate salt or dihydrochloride salt thereof.
 (b) 1,4-Bis[3-(1,3,6,7-tetrahydro-1,3-dioxo-2H-indeno[6,7,1-def]isoquinoline-2-yl)-N-ethyl-propylamino]butane, or the dihydrochloride salt thereof.
 (c) 4-[3-(1,3,6,7-tetrahydro-1,3-dioxo-2H-indeno[6,7,1-def]isoquinoline-2-yl)propylamino]-1-(1,3,6,7-tetrahydro-1,3-dioxo-2H-indeno-[6,7,1-def]isoquinoline-2-yl)butane, or the methanesulfonate salt thereof.

Synthesis

The present invention describes a series of bifunctional naphthalimides containing an ethano bridge across the 4 and 5 positions of the naphthalimide ring that are efficacious against cancer and are more soluble in aqueous media than prior art compounds not containing this bridging group.

Compounds of this invention can be synthesized by reacting two equivalents of an anhydride of Formula (II) with one equivalent of a polyamine of Formula (III) in an inert solvent such as ethanol or dimethylformamide at a temperature ranging from ambient to the solvent's boiling temperature (Scheme I). The resulting suspension can then be filtered to give the free base of (IV) or it can be acidified with the appropriate mineral or organic acid to produce a pharmaceutically acceptable salt, which can be obtained by filtration. Salts of the free base can also be prepared by acidifying a suspension of the free base in ethyl alcohol or dichloromethane with the appropriate mineral or organic acid and collecting the thus formed solid by filtration.

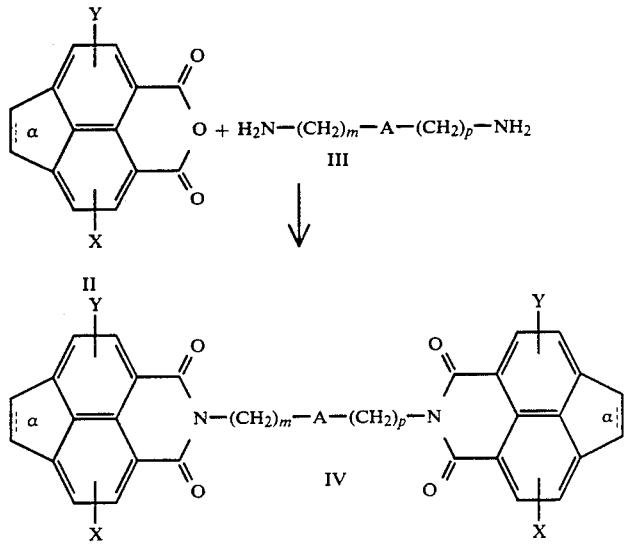

Scheme I

The parent anhydride (II) (X=Y=H, α=single bond) was prepared according to literature procedures (Wyler, M.; Kershaw, A., U.S. Pat. No. 2,072,237 Mar. 2, 1937; Trost, B. M.; Bright, G. M.; Frihart, C.; Brittelli, D. *J. Am. Chem. Soc.* 1971, 93, 737) and derivatives can be prepared by established methods known to those skilled in the art.

Compounds of Formula (III) can be prepared by literature procedures (Bergeron, *Accts. Chem. Res.* 1986, 19, 105; Niitsu, et al. *Chem. Pharm. Bull.* 1986, 34, 1032) and by methods similar to those described herein.

The requisite N,N'-bis-(3-aminopropyl)-N,N'-diethyl-1,4-butanediamine (VI) used for the synthesis of Example 3 was prepared in two steps (Scheme II). Thus, N,N'-diethyl-2-butene-1,4-diamine was reacted with two equivalents of acrylonitrile to give (V). The nitriles and the double bond were reduced by catalytic hydrogenation under standard conditions in succession to give (VI).

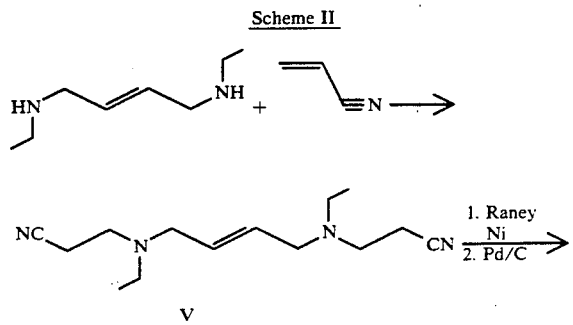

Scheme II

-continued
Scheme II

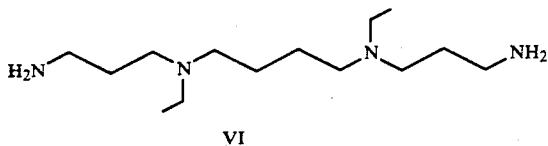

VI

For compounds of Formula (I) where X and Y are different from X' and Y', or X and Y are at different positions on the ring than X' and Y', the synthesis can be achieved by reacting an intermediate of Formula (VIII) with one equivalent of an anhydride of Formula (II) under the same reaction conditions as above. Intermediate (VIII) can be prepared by heating a mixture of one equivalent each of an anhydride of Formula (VII) and the polyamine of Formula (III) in the presence of hydrochloric acid (Scheme III).

Scheme III

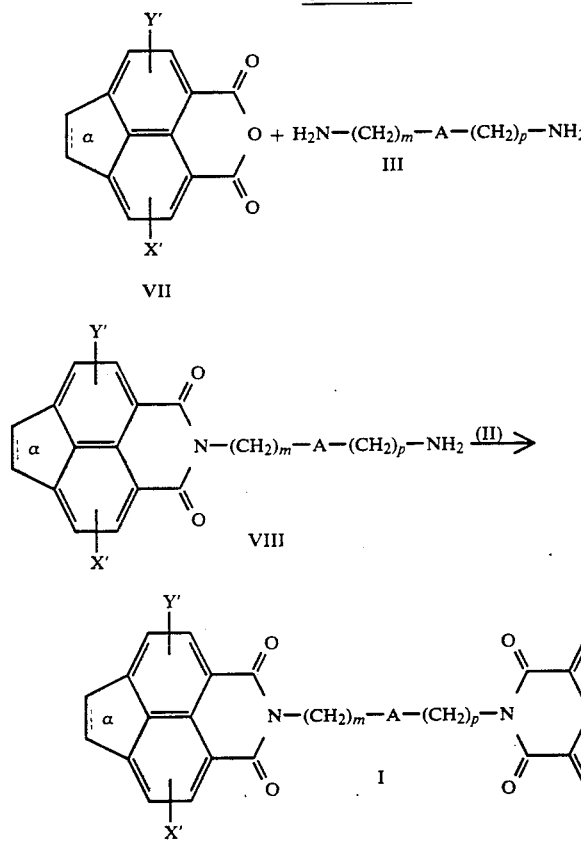

The invention can be further understood by referring to the following examples wherein parts and percentages are by weight unless otherwise specified.

EXAMPLE 1

1,4-Bis-[3-(1,3,6,7-tetrahydro-1,3-dioxo-2H-indeno[6,7,1-def]isoquinoline-2-yl)propyl)-amino]butane dihydromethanesulfonate A mixture of 6,7-dihydroacenaphtho[5,6-cd]pyran-1,3-dione (5.00 g, 22.3 mmol) and spermine (2.02 g, 9.98 mmol) was stirred in dimethylformamide (DMF) (50 mL) at 80° C. for 3 days. The reaction mixture was cooled to room temperature and poured into water. The precipitated solids were stirred in ethanol, collected by filtration, and washed with hexane to give 5.71 g (93%): m.p. 170° C. (d). MS (CI) (m/e) 616 (M+1).

The above solid (1.83 g, 3.0 mmol) was stirred in dichloromethane (200 mL) and methanesulfonic acid (0.4 mL, 6.0 mmol) was added. After being stirred at room temperature for 1 day, the volatiles were evaporated in vacuo. The residue was diluted with dichloromethane (100 mL) and the volatiles evaporated again to give 2.07 g (85%): m.p. 148°–156° C. $^1$H-NMR (200 MHz) (DMSO-$d_6$) $\delta$ 1.75 (br m, 4H), 2.07 (br m, 4H), 3.03 (br m, 8H), 3.95 (s, 6H), 4.12 (br s, 4H), 7.71 (d, 4H), 8.30 (d, 4H), 8.30–8.52 (br m, 4H). IR KBr 1642 cm$^{-1}$ MS (CI) (m/e) 616 (M+1). Anal. Calculated for $C_{38}H_{38}N_4O_4 \cdot 2$ $CH_3SO_3H$: C,64.68; H,6.24; N,7.54. Found: C,64.99; H,6.50; N,7.21.

EXAMPLE 2

1.4-Bis-[3 3.6 7-tetrahydro-1.3-dioxo-2H-indeno[6,7,1-def]isoquinoline-2-yl)propyl-amino]butane dihydrochloride A mixture of 6,7-dihydroacenaphtho[5,6-cd]pyran-1,3-dione (0.5 g, 2.23 mmol) and spermine (0.23 g, 1.16 mmol) was heated to reflux in ethanol (15 mL) for 2.5 h. The suspension was cooled and concentrated hydrochloric acid (2 mL) was added. The resulting suspension was heated to reflux for 16 hr. and cooled to room temperature. The suspended solids were collected by suction filtration and dried to give 0.65 g of a tan solid. This material was heated in ethanol (15 mL) for 20 min, filtered hot, and the collected solid dried to give 0.61 g (79%) of a tan solid: m.p. 225°–230° C (d). $^1$H-NMR (200 MHz, TFA-d) δ 2.03-2.23 (br m, 4H), 2.33-2.60 (br m, 4H), 3.27-3.57 (br m, 8H), 3.65 (s, 8H), 4.40-4.60 (br m, 4H), 7.40-7.67 (br m, 3H), 7.70 (d, 4H, J=7.3 Hz), 8.62 (d, 4H, J=7.3 Hz). IR (nujol) 1700, 1665, 1635, 1415, 1380, 1345, 1250, 780 cm$^{-1}$ MS (CI) (m/e, %) 615 (M+1, free base, 100), 333 (9), 281 (3).

EXAMPLE 3

Part A.
N,N'-(2-cyanoethyl)-N,N'-diethyl-2-butene-1,4-diamine (Formula V))

Acrylonitrile (20 mL, 303.8 mmol) was added dropwise to a stirred solution of N,N'-diethyl-2-butene-1,4-diamine (20 g, 140.6 mmol) in 50 mL of anhydrous ethanol. The solution was stirred at room temperature for 48 hr. The solvent and excess of acrylonitrile were removed by in vacuo rotary evaporation and the residue was dried in vacuo to give (V) as a yellow liquid (34.09 g, 97.6% yield). $^1$H-NMR (CDCl$_3$) δ 5.67 (m, 2H, CH=CH), 3.13 (d of d, 4H, Jab=1.5 Hz, Jac=3.2 Hz, 2 CH$_2$CH=), 2.79 (t, 4H, J=6.9 Hz, 2 NCH$_2$CH$_2$CN), 2.57 (q, 4H, J=7.1 Hz, 2CH$_2$CH$_3$), 2.45 (t, 4H, J=6.9 Hz, 2 CH$_2$CN) and 1.05 (t, 6H, J=7.1 Hz, 2 CH$_3$). IR (neat) 2247 (CN) cm$^{-1}$. MS Mass Calculated for C$_{14}$H$_{24}$N$_4$: 248 2001. Found: 248.1999.

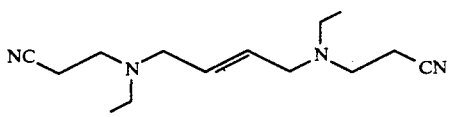

Part B.
N,N'-bis(3-aminopropyl)-N,N'-diethyl-1,4-butanenediamine (Formula (VI))

3.6 g of Raney nickel and 6.0 mL of 50% aqueous sodium hydroxide were added to a 95% ethanolic solution (120 mL) of (V) (15 g). The mixture was hydrogenated at room temperature for 2 days. A total of 256 psi of hydrogen was consumed. The catalyst was removed by filtration and the filtrate was evaporated in vacuo to give 14.49 g of a pink liquid, whose NMR spectrum indicated the presence of <10% of olefin remaining. This material was dissolved in 100 mL of absolute ethanol and 1.5 g of 10% palladium on carbon was added. The mixture was hydrogenated at room temperature overnight consuming 9 psi of hydrogen. The catalyst was removed by filtration with the aid of Celite ® and the filtrate evaporated to give (VI) as a light yellow liquid, 14.03 g (89.6% yield). $^1$H-NMR (CDCl$_3$) δ 2.73 (t, 4H, J=7.0 Hz, 2 CH$_2$N), 2.51 (q, 4H, J=7.0 Hz, 2 CH$_2$CH$_3$), 2.46 (t, 4H, J=7.0 Hz, 2 CH$_2$N), 2.42 (m, 4H, 2 NH$_2$), 1.59 (quintet, 4H, J=7.0 Hz, 2 CH$_2$N), 1.42 (m, 8H, 4 CH$_2$) and 1.01 (t, 6H, J=7.0 Hz, 2 CH$_3$). IR (neat) 3362, 3289 (NH$_2$) cm$^{-1}$. HRMS calculated for C$_{14}$H$_{34}$N$_4$: 258.2783. Found: 258.2783.

Part C.
1,4-Bis-3-(1,3,6,7-tetrahydro-1,3-dioxo-2H-indeno6,7,1-def]isoquinoline-2-yl)-N-ethyl-propylamino]butane dihydrochloride A mixture of 6,7-dihydroacenaphtho[5,6-cd]pyran-1,3-dione (0.95 g, 4.23 mmol) and the amine (VI) (0.55 g, 2.12 mmol) in 50 mL of anhydrous ethanol was stirred under nitrogen at room temperature for 1 hr. and heated to reflux overnight. The solids were collected by filtration, washed with ethanol, and dried under vacuum to give 1.19 g (83.7% yield), of the free base. m.p. 178°-180° C. MS (CI) (m/e) 671 (M+1).

The free base was stirred overnight at room temperature in 25 mL of absolute ethanol containing 4.5 mL of concentrated hydrochloric acid. The light green solids were collected by filtration, washed with warm ethanol and dried under vacuum at 78° C. to give the hydrochloride salt, 0.89 g (61.4% yield). m.p. 255°-257° C. (dec). $^1$H-NMR (D$_2$O) δ 7.10 (d, 4H, J=7.5 Hz, 4 aromatic protons), 6.66 (d, 4H, 4 aromatic protons), 3.44 (m, 4H, 2 CH$_2$NCO), 3.18 (m, 12H, 6 CH$_2$N), 2 70 (s, 8H, 4 CH$_2$), 1.75 (m, 8H, 4 CH$_2$) and 1.20 (t, 6H, J=7.0 Hz, 2 CH$_3$). IR (KBr) 3430 (NH), 1693, 1655 (imide) cm$^{-1}$. MS (CI) (m/e) 671 (M+1,free base). Anal. Calculated. for C$_{42}$H$_{46}$N$_4$O$_4$.2 HCl H$_2$O (MW 761.79): C,66.21; H,6.62; N,7.35. Found: C,66.00, 66.17; H,6.50,6.26; N,7.33,7.43.

EXAMPLE 4

4-3-(1,3,6,7-Tetrahydro-1,3-dioxo-2H-indeno6,7,1-def]isoquinoline-2-yl)propyl-amino1-1-(1,3,6,7-tetrahydro-1,3-dioxo-2H-indeno-6,7,1-def]isoquinoline-2-yl)butane methanesulfonate A mixture of 6,7-dihydroacenaphtho[5,6-cd]pyran-1,3-dione (1.0 g, 4.46 mmol) and spermidine (0.33 g, 2.27 mmol) in 75 mL of anhydrous ethanol was stirred at room temperature and then heated to reflux overnight. The solids were collected by filtration, washed with warm ethanol, and dried under vacuum at 78° C. to give the free base, 0.89 g (70.3% yield). m.p. 238°-241° C.

The free base was stirred overnight at room temperature in 25 mL of dichloromethane containing 0.25 g of (2.6 mmol) of methanesulfonic acid. The solvents were evaporated and the separated solids were treated with ethyl ether, filtered, and dried under vacuum to give the methanesulfonate, 1.12 g (54.8% yield). m.p. 97°-99° C. (dec). $^1$H-NMR (TFA-d) δ 8.85 (d, 4H, J=7.5 Hz, aromatic protons), 7.95 (d, 4H, aromatic protons), 7.40 (broad, 2H, +NH$_2$), 4.70 (m, 4H, 2 CH$_2$NCO), 3.88 (s, 8H, 4 CH$_2$), 3.60 (m, 4H, 2 CH$_2$N), 3.38 (s, 9H, 3 CH$_3$SO$_3$H), 2.68 (m, 2H, CH$_2$) and 2.30 (m, 4H, 2 CH$_2$). IR (KBr) 343C, 51.56,51.77; H,5.05,5.03; N,4.88,4.87; S,9.58,9.51.

TABLE 1

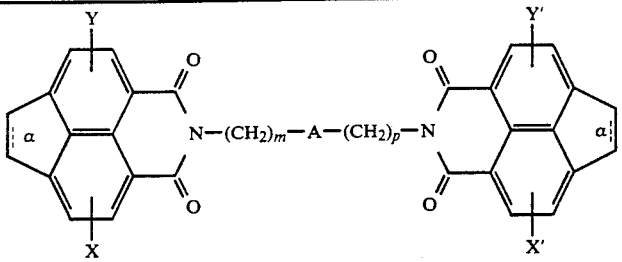

| Ex | X | Y | X' | Y' | a* | m | p | A | Salt | mp °C. |
|---|---|---|---|---|---|---|---|---|---|---|
| 1 | H | H | H | H | S | 3 | 3 | NH(CH$_2$)$_4$NH | CH$_3$SO$_3$H | 148–156 |
| 2 | H | H | H | H | S | 3 | 3 | NH(CH$_2$)$_4$NH | HCl | 225–230(d) |
| 3 | H | H | H | H | S | 3 | 3 | NEt(CH$_2$)$_4$NEt | HCl | 255–257(d) |
| 4 | H | H | H | H | S | 3 | 4 | NH | CH$_3$SO$_3$H | 97–99(d) |
| 5 | NO$_2$ | H | NO$_2$ | H | S | 3 | 4 | NH | CH$_3$SO$_3$H | |
| 6 | NO$_2$ | NO$_2$ | NO$_2$ | NO$_2$ | S | 3 | 4 | NH | CH$_3$SO$_3$H | |
| 7 | NO$_2$ | H | H | H | S | 3 | 4 | NH | CH$_3$SO$_3$H | |
| 8 | H | H | H | H | D | 3 | 4 | NH | CH$_3$SO$_3$H | |
| 9 | H | H | H | H | D | 3 | 3 | NH(CH$_2$)$_4$NH | CH$_3$SO$_3$H | |
| 10 | H | H | H | H | S | 4 | 4 | NH(CH$_2$)$_4$NH | CH$_3$SO$_3$H | |
| 11 | OH | OH | OH | OH | S | 3 | 3 | NH(CH$_2$)$_{10}$NH | CH$_3$SO$_3$H | |
| 12 | OH | OH | OH | OH | D | 4 | 3 | NH(CH$_2$)$_4$NH | CH$_3$SO$_3$H | |
| 13 | OH | OH | OH | OH | S | 4 | 3 | NH(CH$_2$)$_2$NH | CH$_3$SO$_3$H | |
| 14 | OH | OH | OH | OH | S | 3 | 4 | NH(CH$_2$)$_4$NH | CH$_3$SO$_3$H | |
| 15 | OCH$_3$ | OCH$_3$ | OCH$_3$ | OCH$_3$ | D | 3 | 3 | NH(CH$_2$)$_4$NH | CH$_3$SO$_3$H | |
| 16 | OCH$_3$ | OCH$_3$ | OCH$_3$ | OCH$_3$ | S | 3 | 3 | NH(CH$_2$)$_4$NH | CH$_3$SO$_3$H | |
| 17 | OCH$_3$ | OCH$_3$ | OCH$_3$ | OCH$_3$ | S | 3 | 4 | NH(CH$_2$)$_{10}$NH | CH$_3$SO$_3$H | |
| 18 | OCH$_3$ | OCH$_3$ | OCH$_3$ | OCH$_3$ | D | 4 | 3 | NH(CH$_2$)$_2$NH | CH$_3$SO$_3$H | |
| 19 | Br | Br | Br | Br | S | 3 | 3 | NH(CH$_2$)$_4$NH | CH$_3$SO$_3$H | |
| 20 | Br | Br | Br | Br | D | 3 | 3 | NH(CH$_2$)$_4$NH | CH$_3$SO$_3$H | |
| 21 | Br | Br | Br | Br | S | 4 | 3 | NH(CH$_2$)$_4$NH | HCl | |
| 22 | Br | Br | Br | Br | S | 3 | 4 | NH(CH$_2$)$_4$NH | HCl | |
| 23 | Cl | Cl | Cl | Cl | S | 3 | 3 | NH(CH$_2$)$_4$NH | CH$_3$SO$_3$H | |
| 24 | Cl | Cl | Cl | Cl | D | 3 | 3 | NH(CH$_2$)$_4$NH | CH$_3$SO$_3$H | |
| 25 | Cl | Cl | Cl | Cl | S | 4 | 3 | NH(CH$_2$)$_6$NH | CH$_3$SO$_3$H | |
| 26 | Cl | Cl | Cl | Cl | D | 3 | 4 | NH(CH$_2$)$_4$NH | CH$_3$SO$_3$H | |
| 27 | NH$_2$ | NH$_2$ | NH$_2$ | NH$_2$ | S | 3 | 3 | NH(CH$_2$)$_2$NH | CH$_3$SO$_3$H | |
| 28 | NH$_2$ | NH$_2$ | NH$_2$ | NH$_2$ | S | 3 | 3 | NH(CH$_2$)$_4$NH | CH$_3$SO$_3$H | |
| 29 | NH$_2$ | NH$_2$ | NH$_2$ | NH$_2$ | S | 3 | 3 | NEt(CH$_2$)$_4$NEt | CH$_3$SO$_3$H | |
| 30 | NH$_2$ | NH$_2$ | NH$_2$ | NH$_2$ | S | 3 | 4 | NH(CH$_2$)$_{10}$NH | CH$_3$SO$_3$H | |
| 31 | NMe$_2$ | NMe$_2$ | NMe$_2$ | NMe$_2$ | S | 3 | 3 | NH(CH$_2$)$_4$NH | CH$_3$SO$_3$H | |
| 32 | NMe$_2$ | NMe$_2$ | NMe$_2$ | NMe$_2$ | D | 2 | 6 | NH(CH$_2$)$_6$NH | CH$_3$SO$_3$H | |
| 33 | NMe$_2$ | NMe$_2$ | NMe$_2$ | NMe$_2$ | S | 3 | 4 | NH(CH$_2$)$_4$NH | CH$_3$SO$_3$H | |
| 34 | NMe$_2$ | NMe$_2$ | NMe$_2$ | NMe$_2$ | D | 4 | 3 | NH(CH$_2$)$_4$NH | CH$_3$SO$_3$H | |
| 35 | H | NH$_2$ | H | NH$_2$ | S | 3 | 3 | NH(CH$_2$)$_4$NH | CH$_3$SO$_3$H | |
| 36 | NH$_2$ | NH$_2$ | H | H | S | 3 | 3 | NH(CH$_2$)$_2$NH | CH$_3$SO$_3$H | |
| 37 | NH$_2$ | NH$_2$ | H | H | D | 3 | 4 | NH(CH$_2$)$_4$NH | CH$_3$SO$_3$H | |
| 38 | NH$_2$ | NH$_2$ | H | H | D | 4 | 4 | NH(CH$_2$)$_{10}$NH | CH$_3$SO$_3$H | |
| 39 | H | NMe$_2$ | H | NMe$_2$ | S | 3 | 3 | NH(CH$_2$)$_4$NH | CH$_3$SO$_3$H | |
| 40 | NMe$_2$ | NMe$_2$ | H | H | S | 3 | 3 | NH(CH$_2$)$_6$NH | CH$_3$SO$_3$H | |
| 41 | NEt$_2$ | NEt$_2$ | NEt$_2$ | NEt$_2$ | S | 3 | 3 | NH(CH$_2$)$_4$NH | CH$_3$SO$_3$H | |
| 42 | NEt$_2$ | NEt$_2$ | NEt$_2$ | NEt$_2$ | S | 3 | 4 | NH(CH$_2$)$_2$NH | CH$_3$SO$_3$H | |
| 43 | NEt$_2$ | NEt$_2$ | NEt$_2$ | NEt$_2$ | D | 4 | 4 | NH(CH$_2$)$_6$NH | CH$_3$SO$_3$H | |
| 44 | NEt$_2$ | NEt$_2$ | NEt$_2$ | NEt$_2$ | D | 3 | 3 | NH(CH$_2$)$_4$NH | CH$_3$SO$_3$H | |
| 45 | NEt$_2$ | NEt$_2$ | H | H | S | 3 | 3 | NH(CH$_2$)$_4$NH | CH$_3$SO$_3$H | |
| 46 | NEt$_2$ | H | NEt$_2$ | H | S | 3 | 4 | NH(CH$_2$)$_4$NH | CH$_3$SO$_3$H | |
| 47 | NEt$_2$ | H | NEt$_2$ | H | D | 4 | 4 | NH(CH$_2$)$_6$NH | CH$_3$SO$_3$H | |
| 48 | OC$_6$H$_{13}$ | OC$_6$H$_{13}$ | OC$_6$H$_{13}$ | OC$_6$H$_{13}$ | S | 3 | 3 | NH(CH$_2$)$_4$NH | CH$_3$SO$_3$H | |
| 49 | OC$_6$H$_{13}$ | OC$_6$H$_{13}$ | OC$_6$H$_{13}$ | OC$_6$H$_{13}$ | S | 4 | 4 | NH(CH$_2$)$_4$NH | CH$_3$SO$_3$H | |
| 50 | OC$_6$H$_{13}$ | OC$_6$H$_{13}$ | OC$_6$H$_{13}$ | OC$_6$H$_{13}$ | S | 3 | 4 | NH(CH$_2$)$_2$NH | CH$_3$SO$_3$H | |

*S = single bond; D = double bond

Utility

Results of the biological test described below establish that the compounds of this invention have the property of activating nonspecific immune cells, such as natural killer (NK) cells and macrophages, to kill tumor cells in mice.

One common route of cancer spread is through the blood. Very few cancer cells survive this hostile environment to go on and form metastases; NK cells and macrophages are believed to play an important role in controlling this hematogenous spread (Hanna, N. Cancer Research, 42:1337, 1982). Following the injection of various immunomodulators, macrophages and NK cells can be removed and shown to kill tumor cells in tissue culture. These same immunomodulators have also been shown to inhibit the growth of transplanted mouse tumors, presumably by their activation of macrophages and NK cells in vivo. In the tumor cell clearance assay detailed below, radiolabelled tumor cells are injected intravenously (i.v.) into mice injected with an immunomodulator one day earlier. A decreased number of tumor cells, as reflected by a decreased amount of radioactivity remaining in the lungs, is used as an endpoint.

Tumor Cell Clearance Test B16F10 Melanoma

The B16 tumor line established from melanoma tumor which arose spontaneously on the skin at the base of the ear in a C57BL mouse. The B16F10 tumor subline was derived from the parent B16 line by selection for its ability to form lung tumors in vitro after i.v. injection and was subsequently established in vitro after 10 cycles of lung metastasis formation (Fidler, *Eur. J. Cancer* 9:223, 1973). The B16F10 tumor line is maintained by serial passage in vitro.

On day 0 female mice are injected intraperitoneally (i.p.) with test compound (6 mice/group) or vehicle alone (10 mice/group). Twenty-four hours later all mice are injected intravenously with 100,000 [$^{125}$I] Iododeoxyuridine labelled B16F10 melanoma cells in 0.2 mL. Eighteen hours later mice are sacrificed and lungs removed and counted on a gamma counter.

Control and experimental group mean values are compared to the vehicle control using a Student's t-test. Poly I:C is an immunostimulant which activates macrophages and NK cells to kill and clear tumor cells faster and thus results in fewer cpm/lung. Statistical significance is set at $p<0.05$, and compounds with treated/control (T/C) values of $<0.40$ are considered positive.

Results with the compound of Example 3 and Poly I:C are shown in Table I. The data indicate that the compound of Example 3 is effective in activating nonspecific immune cells against the B16F10 melanoma.

TABLE I

| Dose Group | N | (mg/kg) | CPM/Lung (Mean + SEM) | Treated/Control |
|---|---|---|---|---|
| Vehicle Control | 10 | — | 31069 + 1979 | 1.00 |
| Untreated Control | 6 | — | 31227 + 2296 | 1.01 |
| Poly I:C | 6 | 5 | 1044 + 87 | 0.03* |
| Example 3 | 6 | 6.25 | 27953 + 2567 | 0.90 |
|  | 6 | 12.5 | 24905 + 2497 | 0.80 |
|  | 6 | 25 | 6992 + 1417 | 0.23* |
|  | 6 | 50 | 3558 + 476 | 0.11* |

*p < 0.001 compared to vehicle control

Tissue Culture

L1210 cells were maintained in RPM-1640 a medium supplemented with 10% heat inactivated fetal bovine serum and 50 mL mercaptomethanol/liter medium (RPMI-L). B16 cells were maintained in RPMI-1640 medium supplemented with 15% heat inactivated fetal bovine serum and antibiotics (RPMI-C).

In vitro Growth Inhibitory Activity Determination

Exponential growing L1210 cells ($1\times10^3$ cells) or B16 cells ($2-3\times10^3$ cells) in 0.1 mL medium were seeded on day 0 in a 96-well microtiter plate. On day 1, 0.1 mL aliquot of medium containing graded concentration of test analogs was added to the initial volume. After incubation at 37° C. in a humidified incubator for 3 days, the plates were centrifuged briefly and 100 mL of the growth medium was removed. Cell cultures were incubated with 50 mL of 3-(4,5-dimethylthiazol-2-yl)-2,5-diphenyltetrazolium bromide (MTT; 1 mg/ml in Dulbecco's phosphate buffer saline) for 4 hr. at 37° C. The resulting purple formazan precipitate was solubilized with 200 mL of 0.04 N HCl in isopropyl alcohol. Absorbance was read in a Titertek Multiskan MCC scanning well spectrophotometer (Flow Laboratories) at a test wavelength of 570 nm and a reference wavelength of 630 nm.

Data Analysis

The absorbances were stored on a floppy disk on a IBM-XT and uploaded on to a VAX computer. The ID$_{50}$ values were determined by a computer program that fit all of the data (8 determinations per concentration and 12 concentrations per test analog) to the following equation:

$$Y=((Am-Ao)/(1+(X/ID_{50})n))+Ao$$

where
- Am = absorbance of the control cells
- Ao = absorbance of the cells in the presence of highest drug conc.
- Y = observed absorbance
- X = drug concentration
- ID$_{50}$ = dose of drug that inhibits the growth of cells to one half that of the control cells Results are shown in Table II.

TABLE II

| Examples | ID$_{50}$ (L1210) |
|---|---|
| 1 | 3.01 μM |
| 2 | 1.72 μM |
| 3 | 0.022 μM |
| 4 | 0.29 μM |

Dosage Forms

The antitumor compounds (active ingredients) of this invention can be administered to inhibit tumors by any means that produces contact of the active ingredient with the agent's site of action in the body of a mammal. They can be administered by any conventional means available for use in conjunction with pharmaceuticals; either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a tumor-inhibiting amount of active ingredient and will, of course, vary depending upon known factors such as the pharmacodynamic characteristics of the particular active ingredient, and its mode and route of administration; age, health, and weight of the recipient; nature and extent of symptoms; kind of concurrent treatment, frequency of treatment, and the effect desired. Usually a daily dosage of active ingredient can be about 5 to 400 milligrams per kilogram of body weight. Ordinarily, 10 to 200, and preferably 10 to 50, miligrams per kilogram per day sustained release form is effective to obtain desired results.

Dosage forms (compositions) suitable for internal administration contain from about 1.0 milligram to about 500 milligrams of active ingredient per unit. In these pharmaceutical compositions, the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tables and capsules can be manufactured as sustained release products to provide for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration can contain coloring and flavoring to increase protein acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined and suitable stabilizing agents. Also used are citric acid and its salts and sodium EDTA. In addition, parenteral solution can contain preservatives, such as benzalkonium chloride, methyl- or propyl-paraben, and chlorbutanol.

Suitable pharmaceutical carriers are described in *Remington's Pharmaceutical Sciences*, A. Osol, (1985) 17th Edition, a standard reference text in this field.

Useful pharmaceutical dosage forms for administration of the compounds of this invention can be illustrated as follows:

Capsules

A large number of unit capsules are prepared by filling standard two-piece hard gelatin capsules each with 100 milligrams of powdered active ingredient, 175 milligrams of lactose, 24 milligrams of talc, and 6 milligrams magnesium stearate.

A mixture of active ingredient in soybean oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or delay.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

"Consisting essentially of" in the present disclosure is intended to have its customary meaning: namely, that all specified material and conditions are very important in practicing the invention but that unspecified materials and conditions are not excluded so long as they do not prevent the benefits of the invention from being realized.

What is claimed is:

1. A compound of the formula:

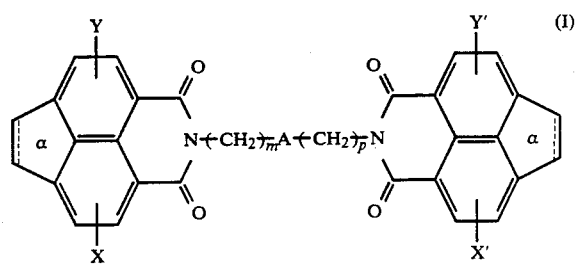

or a pharmaceutically acceptable salt thereof, wherein:

A is $RN(CH_2)_nNR'$ or $NR^1$ (n=2-10);

R, R' and $R^1$ independently are H, $C_1-C_6$ alkyl, benzyl optionally substituted with 1 or more substituents independently selected from the group consisting of:

H, $C_1-C_6$ alkyl, halogen, $CF_3$, $NO_2$, OH, $N(R^2)_2$, $OR^3$, $CO_2R^4$, $CONR^5$, $NHCOR^6$, $SO_2NR^7$ or $S(O)_tR^8$, (t is 0, 1 or 2);

$R^2$, $R^5$ and $R^7$ independently are H, $C_1-C_3$ alkyl including cyclopropyl;

$R^3$ and $R^4$ independently are H or $C_1-C_6$ alkyl;

$R^6$ and $R^8$ independently are $C_1-C_6$ alkyl;

X, X', Y and Y' independently are selected from the group consisting of:

H, $NO_2$, $N(R^9)_2$, halogen or $OR^{10}$;

$R^9$ and $R^{10}$ independently are H Or $C_1-C_6$ alkyl;

each α is independently a single or a double bond; and m and p independently are 2-10.

2. A compound of claim 1 wherein A is $RN(CH_2)_nNR'$.

3. A compound of claim 1 wherein R and R' are $C_1$ to $C_6$ alkyl.

4. A compound of claim 1 wherein n is 2-6.

5. A compound of claim 2 wherein n is 2-6.

6. A compound of claim 1 wherein m and p independently are 2-6.

7. A compound of claim 1 wherein X, X', Y and Y' are H.

8. A compound of claim 1 wherein each α is a single bond.

9. A compound of claim 1 wherein:

A is $RN(CH_2)_nNR'$;

R and R' are independently $C_1-C_6$ alkyl;

n is 2-6;

m and p are independently 2-6;

X, X', Y and Y' are H; and each α is a single bond.

10. The compound of claim 1 which is 1,4-Bis-[3-(1,3,6,7-tetrahydro-1,3-dioxo-2H-indeno[6,7,1-def]isoquinoline-2-yl)propyl-amino]butane, or the dihydromethane sulfonate salt or dihydrochloride salt thereof.

11. The compound of claim 1 which is 1,4-Bis[3-(1,3,6,7-tetrahydro-1,3-dioxo-2H-indeno[6,7,1-def-]isoquinoline-2-yl)-N-ethyl-propylamino]butane, or the dihydrochloride salt thereof.

12. The compound of claim 1 which is 4-[3-(1,3,6,7-tetrahydro-1,3-dioxo-2H-indeno[6,7,1-def]isoquinoline-2-yl)propyl-amino]-1-(1,3,6,7-tetrahydro-1,3-dioxo-2H-indeno-[6,7,1-def]isoquinoline-2-yl)butane, or the methanesulfonate salt thereof.

13. A pharmaceutical composition comprising a pharmaceutically acceptable carrier and a therapeutically effective amount of a compound of claim 1.

14. A pharmaceutical composition comprising a pharmaceutically acceptable carrier and a therapeutically effective amount of a compound of claim 2.

15. A pharmaceutical composition comprising a pharmaceutically acceptable carrier and a therapeutically effective amount of a compound of claim 3.

16. A pharmaceutical composition comprising a pharmaceutically acceptable carrier and a therapeutically effective amount of a compound of claim 4.

17. A pharmaceutical composition comprising a pharmaceutically acceptable carrier and a therapeutically effective amount of a compound of claim 5.

18. A pharmaceutical composition comprising a pharmaceutically acceptable carrier and a therapeutically effective amount of a compound of claim 6.

19. A pharmaceutical composition comprising a pharmaceutically acceptable carrier and a therapeutically effective amount of a compound of claim 7.

20. A pharmaceutical composition comprising a pharmaceutically acceptable carrier and a therapeutically effective amount of a compound of claim 8.

21. A pharmaceutical composition comprising a pharmaceutically acceptable carrier and a therapeutically effective amount of a compound of claim 9.

22. A pharmaceutical composition comprising a pharmaceutically acceptable carrier and a therapeutically effective amount of the compound of claim 10.

23. A pharmaceutical composition comprising a pharmaceutically acceptable carrier and a therapeutically effective amount of the compound of claim 11.

24. A pharmaceutical composition comprising a pharmaceutically acceptable carrier and a therapeutically effective amount of the compound of claim 12.

25. A method of treating a B16F10 melanoma tumor in a mammal comprising administering to the mammal bearing such tumor, a tumor-inhibiting amount of claim 1.

26. A method of treating a B16F10 melanoma tumor in a mammal comprising administering to the mammal bearing such tumor, a tumor-inhibiting amount of claim 2.

27. A method of treating a B16F10 melanoma tumor in a mammal comprising administering to the mammal bearing such tumor, a tumor-inhibiting amount of claim 3.

28. A method of treating a B16F10 melanoma tumor in a mammal comprising administering to the mammal bearing such tumor, a tumor-inhibiting amount of claim 4.

29. A method of treating a B16F10 melanoma tumor in a mammal comprising administering to the mammal bearing such tumor, a tumor-inhibiting amount of claim 5.

30. A method of treating a B16F10 melanoma tumor in a mammal comprising administering to the mammal bearing such tumor, a tumor-inhibiting amount of claim 6.

31. A method of treating a B16F10 melanoma tumor in a mammal comprising administering to the mammal bearing such tumor, a tumor-inhibiting amount of claim 7.

32. A method of treating a B16F10 melanoma tumor in a mammal comprising administering to the mammal bearing such tumor, a tumor-inhibiting amount of claim 8.

33. A method of treating a B16F10 melanoma tumor in a mammal comprising administering to the mammal bearing such tumor, a tumor-inhibiting amount of claim 9.

34. A method of treating a B16F10 melanoma tumor in a mammal comprising administering to the mammal bearing such tumor, a tumor-inhibiting amount of claim 10.

35. A method of treating a B16F10 melanoma tumor in a mammal comprising administering to the mammal bearing such tumor, a tumor-inhibiting amount of claim 11.

36. A method of treating a B16F10 melanoma tumor in a mammal comprising administering to the mammal bearing such tumor, a tumor-inhibiting amount of claim 12.

* * * * *